(12) United States Patent
Hagiwara (10) Patent No.: US 7,783,001 B2
(45) Date of Patent: Aug. 24, 2010

(54) X-RAY CT APPARATUS AND IMAGE RECONSTRUCTING DEVICE

(75) Inventor: Akira Hagiwara, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 143 days.

(21) Appl. No.: 12/335,200

(22) Filed: Dec. 15, 2008

(65) Prior Publication Data

US 2009/0161822 A1 Jun. 25, 2009

(30) Foreign Application Priority Data

Dec. 21, 2007 (JP) .............................. 2007-330246

(51) Int. Cl.
*A61B 6/00* (2006.01)
(52) U.S. Cl. .................................. 378/20; 378/4; 378/8
(58) Field of Classification Search .................. 378/4, 378/8, 15, 20
See application file for complete search history.

(56) References Cited

U.S. PATENT DOCUMENTS

| | | | |
|---|---|---|---|
| 4,034,224 A | 7/1977 | Heavens et al. | |
| 5,046,003 A | 9/1991 | Crawford | |
| 5,262,946 A | 11/1993 | Heuscher | |
| 5,383,231 A | 1/1995 | Yamagishi | |
| 5,928,148 A | 7/1999 | Wang et al. | |
| 6,023,494 A | 2/2000 | Senzig et al. | |
| 6,061,420 A | 5/2000 | Strong et al. | |
| 6,061,422 A * | 5/2000 | Miyazaki et al. | 378/15 |
| 6,185,271 B1 | 2/2001 | Kinsinger | |
| 6,233,478 B1 | 5/2001 | Liu | |
| 6,266,553 B1 | 7/2001 | Fluhrer et al. | |
| 6,442,228 B1 | 8/2002 | Woloschek et al. | |
| 6,466,640 B1 | 10/2002 | Taguchi | |
| 6,504,893 B1 | 1/2003 | Flohr et al. | |
| 6,535,821 B2 | 3/2003 | Wang et al. | |
| 2002/0131544 A1* | 9/2002 | Aradate et al. | 378/4 |
| 2003/0163039 A1 | 8/2003 | Pan et al. | |
| 2004/0017881 A1* | 1/2004 | Cesmeli et al. | 378/4 |
| 2004/0174960 A1* | 9/2004 | Hsieh et al. | 378/210 |
| 2005/0175140 A1* | 8/2005 | Tsujii | 378/4 |
| 2007/0086563 A1* | 4/2007 | Bruder | 378/8 |

FOREIGN PATENT DOCUMENTS

JP    2003-275200    9/2003

* cited by examiner

*Primary Examiner*—Edward J Glick
*Assistant Examiner*—Alexander H Taningco
(74) *Attorney, Agent, or Firm*—Armstrong Teasdale LLP (57) ABSTRACT

An X-ray CT apparatus includes image reconstructing device which specifies a first imaging range, a second imaging range and a third imaging range located between the first imaging range and the second imaging range in association with each position on a body axis of a subject, image-reconstructs a tomographic image included in the first imaging range using a first projection data amount necessary for image reconstruction of the tomographic image, image-reconstructs a tomographic image included in the second imaging range using a second projection data amount less than the first projection data amount, and image-reconstructs a tomographic image included in the third imaging range using a third projection data amount less than the first projection data amount and greater than the second projection data amount.

20 Claims, 5 Drawing Sheets

X-RAY CT APPARATUS AND IMAGE RECONSTRUCTING DEVICE

CROSS REFERENCE TO RELATED APPLICATIONS

This application claims the benefit of Japanese Patent Application No. 2007-330246 filed Dec. 21, 2007, which is hereby incorporated by reference in its entirety.

BACKGROUND OF THE INVENTION

The subject matter disclosed herein relates to an X-ray CT (Computed Tomography) apparatus and an image reconstructing device for imaging a tomographic image of a subject.

As a chest X-ray CT imaging method, there has heretofore been known a method described in, for example, Japanese Unexamined Patent Publication No. 2003-275200. Namely, the patent document has described the method wherein upon chest X-ray CT photography, a continuous helical scan that X-ray projection data are acquired in a range including the heart while a table is being moved at a relatively slow table velocity, and X-ray projection data are acquired in a range not including the heart while the table is being moved at a relatively fast table velocity, is performed thereby to obtain a tomographic image reduced in motion artifact in a relatively short imaging period of time.

BRIEF DESCRIPTION OF THE INVENTION

Meanwhile, upon general X-ray CT imaging, full reconstruction is carried out which performs image reconstruction using view data related to an angular range of 360°, so-called view data corresponding to a full scan. Upon chest X-ray CT imaging, however, half reconstruction capable of reducing a motion artifact, which performs image reconstruction using view data corresponding to 180°+fan angle, so-called view data corresponding to a half scan, is preferable to the full scan. A tomographic image reconstructed by the half reconstruction has a tendency that the motion artifact is reduced whereas noise increases relatively by the amount of data less than that by the full reconstruction. As described in the patent document 1, a problem arises in that when upon the chest X-ray CT imaging, the helical scan is performed on the range not including the heart and the range including the heart continuously and image reconstruction is performed in the range not including the heart and the range including the heart using different data amounts (range of view data) in terms of the motion artifact, noise characteristics of each tomographic image become discontinuity at the boundary between the range not including the heart and the range including the heart, and when, for example, a chest three-dimensional image is generated using those continuous tomographic images, an artifact occurs in the boundary between the range including the heart and the range not including the heart.

The present invention has been made in view of the above problem. Various embodiments of the present invention provide an X-ray CT apparatus capable of, when, for example, continuous tomographic images are generated using two different amounts of data as in the case where the above-described X-ray CT imaging in the range not including the heart and the range including the heart is performed, reducing discontinuity of image quality such as noise characteristics between the tomographic images at boundary portions thereof.

According to a first aspect of the present invention, there is provided an X-ray CT apparatus comprising scan device including an X-ray source, an X-ray detection unit which includes a plurality of detector elements and detects X rays radiated from the X-ray source, a imaging table which places a subject thereon and disposes the subject between the X-ray source and the X-ray detection unit, a controller which controls the imaging table and both the X-ray source and the X-ray detection unit in such a manner that the X rays are applied thereto from the X-ray source while the imaging table, and the X-ray source and the X-ray detection unit are relatively moved along a body axis of the subject, an X-ray data acquisition section which acquires projection data of the X rays detected by the X-ray detection unit; and image reconstructing device which image-reconstructs a tomographic image of the subject, based on the projection data, wherein the image reconstructing device specifies a first imaging range, a second imaging range and a third imaging range located between the first imaging range and the second imaging range in association with a position on the body axis of the subject, image-reconstructs a tomographic image included in the first imaging range using a first projection data amount corresponding to an amount necessary for image reconstruction of the tomographic image, image-reconstructs a tomographic image included in the second imaging range using a second projection data amount less than the first projection data amount and corresponding to an amount necessary for image reconstruction of the tomographic image, and image-reconstructs a tomographic image included in the third imaging range using a third projection data amount less than the first projection data amount and greater than the second projection data amount.

According to a second aspect of the present invention, there is provided an X-ray CT apparatus wherein in the first aspect, the second range is a range including the heart of the subject, and the first range is a range not including the heart.

According to a third aspect of the present invention, there is provided an X-ray CT apparatus wherein in the first or second aspect, the amount necessary for the image reconstruction of the tomographic image is an amount of data selected from view data from an angular range of 180°+fan angle to an angular range of 360°.

According to a fourth aspect of the present invention, there is provided an X-ray CT apparatus wherein in the third aspect, the first data amount is view data corresponding to the angular range of 360°, and the second data amount is view data corresponding to the angular range of 180°+fan angle.

According to a fifth aspect of the present invention, there is provided an X-ray CT apparatus wherein in any of the first through fourth aspects, the third data amount is set in such a manner that the tomographic image included in the third imaging range is provided in plural form and the amount of projection data decreases continuously from the first range side to the second range side at the tomographic images.

According to a sixth aspect of the present invention, there is provided an X-ray CT apparatus wherein in any of the first through fifth aspects, the controller controls so as to perform the movement of the imaging table relative to the X-ray source and the X-ray detection unit at a velocity V1 in the first range, performs the relative movement at a velocity V2 different from the velocity V1 in the second range, and performs the relative movement by acceleration or deceleration from the velocity V1 to the velocity V2 or from the velocity V2 to the velocity V1.

According to a seventh aspect of the present invention, there is provided an X-ray CT apparatus wherein in the sixth aspect, the controller controls so as to perform the movement of the imaging table relative to the X-ray source and the X-ray detection unit at a velocity V1 in the first range, and performs the relative movement at a velocity V2 lower than the velocity V1 in the second range.

According to an eighth aspect of the present invention, there is provided an X-ray CT apparatus wherein in any of the first through seventh aspects, the first range, the second range and the third range are specified based on a pre-acquired scout image of the subject.

According to a ninth aspect of the present invention, there is provided an X-ray CT apparatus wherein in the eighth aspect, the first range corresponds to each of ranges related to the second range, which adjoin both sides of the subject as viewed in the direction of the body axis thereof.

According to an X-ray CT apparatus of the present invention, when, for example, continuous tomographic images are generated using two different amounts of data as in the case where X-ray CT imaging in a range not including the heart and a range including the heart is performed, discontinuity of image quality such as noise characteristics between the tomographic images at boundary portions thereof can be reduced.

DETAILED DESCRIPTION OF THE INVENTION

Various embodiments of the present invention will be described in detail in accordance with reference to the accompanying drawings.

Figure 1:
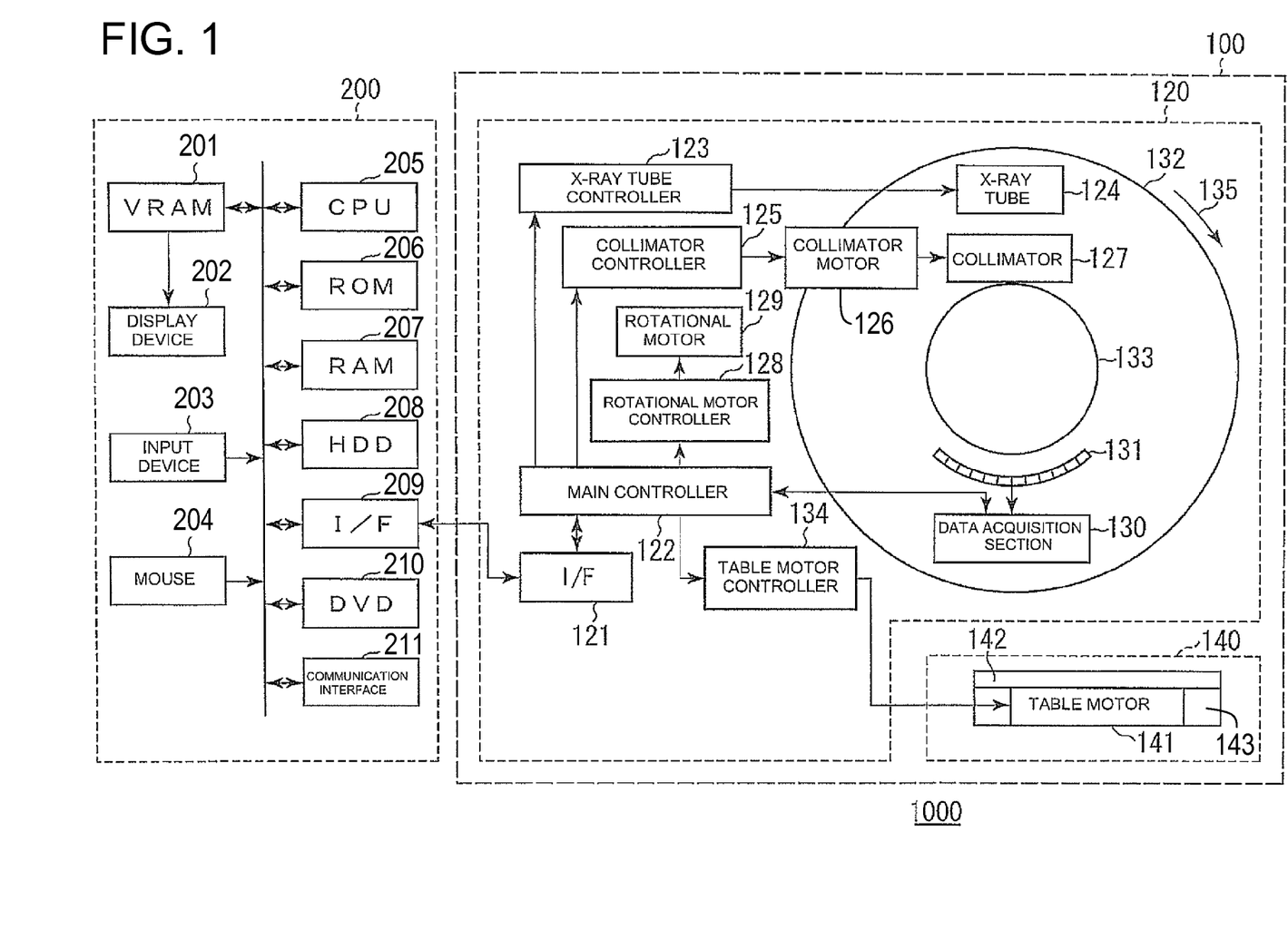
FIG. 1 is a block schematic diagram of an X-ray CT apparatus according to an embodiment.

FIG. 1 is a system configuration diagram of an X-ray CT apparatus 1000 according to one embodiment of the present invention. As shown in FIG. 1, the X-ray CT apparatus 1000 comprises a gantry 120 for detecting the irradiation of a subject (patient) with X rays and the X rays penetrated or transmitted through the subject, an operation console 200 which transmits an instruction signal to the gantry 120 to perform various settings and which reconstructs a tomographic image, based on projection data outputted from the gantry 120 and displays the same, and a conveying device 140 which places the subject thereon and conveys it to the inside of the gantry 120.

The gantry designated at 120 has the following configuration starting with a main controller (control unit) 122 which conducts its entire control. Reference numeral 121 indicates an interface for performing communication with the operation console 200, reference numeral 132 indicates a gantry rotating section, which is provided thereinside with an X-ray tube 124 (driven and controlled by an X-ray tube controller 123) which generates a conebeam X-ray, a collimator 127 which defines the range of irradiation or application of X rays, and a collimator motor 126 which adjusts a slit width for defining the X-ray irradiation range of the collimator 127 and adjusts the position of the collimator 127 in its Z-axis direction (direction orthogonal to the drawing, i.e., a body-axis direction of the subject and direction in which a cradle 142 to be described later is conveyed to an aperture or cavity section 133). The driving of such a collimator motor 126 is controlled by a collimator controller 125. The thickness th of the conebeam X-ray 400 applied to the subject is adjusted according to the degree of aperture of the collimator 127.

The gantry rotating section 132 also has an X-ray detection unit 131 which detects X rays penetrated through the subject, and a data acquisition section 130 which acquires projection data obtained by the X-ray detection unit 131. Incidentally, the X-ray detection unit 131 is configured as a detector array in which detector rows each having a detecting element group comprised of a plurality of detector or detecting elements (channels) are arrayed in an X-axis direction and the Z-axis direction in plural form.

The respective detector elements of the X-ray detection unit 131 respectively supply independent attenuation signals to the data acquisition section 130 comprising a multichannel data acquisition system (DAS). The data acquisition section 130 samples the independent signals of the respective detector elements at a sampling rate determined by a sampling rate clock. Generally, the sampling rate clock is adjusted in such a manner that a desired angular interval is given or made between projections of a tomographic projection set acquired where the sampling rate of each attenuation signal is given as each of different gantry rotational velocities. In short, the gantry rotational velocity can be changed to control a scan time. Each of the so-sampled attenuation signals is brought into digital form and transferred to the main controller 122 as a DAS count corresponding to raw attenuation data. An operator is able to designate the rate of a sampling rate clock corresponding to a desired scan speed using input devices (203 and 204) of the operation console 200.

The X-ray tube 124 and the collimator 127 and the X-ray detection unit 131 are provided at positions opposite to each other with the cavity section 133 interposed therebetween. The gantry rotating section 132 is rotated in the direction indicated by arrow 135 in a state in which the above relationship has been maintained. This rotation is done by a rotational motor 129 whose rotational speed is controlled in a predetermined control cycle by a drive signal outputted from a rotational motor controller 128.

The imaging table 140 has the cradle 142 for actually placing the subject thereon, and a holding table 143 for holding the cradle 142. The cradle 142 is driven in the Z-axis direction (i.e., in a conveying direction of a table=Z-axis direction=body-axis direction of subject) by the table motor 141. The driving of the table motor 141 is done in such a manner that its conveying velocity is controlled in a predetermined control cycle, based on a drive signal outputted from a table motor controller 134.

The main controller 122 analyzes various instruction signals received via the I/F 121 and outputs various control signals to the X-ray tube controller 123, collimator controller 125, rotational motor controller 128, table motor controller 134 and data acquisition section 130, based on the instruction signals. The main controller 122 also performs a process for sending projection data acquired by the data acquisition section 130 to the operation console 200 via the I/F 121.

Incidentally, scan device of the present invention corresponds to a scan device 100 including the X-ray source 124, X-ray detection unit 131, imaging table 140, main controller (control unit) 122 and data acquisition section 130.

The operation console 200 is of a so-called work station and has the following configuration starting with a CPU 205 which conducts control of the entire apparatus, a ROM 206 which stores a boot program or the like therein and a RAM 207 which functions as a main memory as shown in the drawing.

An HDD 208 is of a hard disk drive. Here, the HDD 208 supplies various instructions to the CPU 205 in addition to an OS and a scan control program and stores therein an image reconstruction program for reconstructing an X-ray tomographic image, based on data received by the CPU 205. A VRAM 201 is of a memory for developing image data (256× 256 pixels) to be displayed. Here, the X-ray tomographic image can be displayed on a display device 202 by developing the image data or the like. Reference numeral 203 indicates an input device comprising a keyboard for performing various settings and a mouse or the like. Reference numeral 209 indicates an interface for performing communication with the gantry 120.

The operation console 200 is equipped with a various recording media drive device 210 such as a CD-ROM drive or the like for loading programs and data stored in various recording mediums such as an optical disk, an optical magnetic disk, a CR-ROM, a DVD, a magnetic tape, a nonvolatile memory card, etc. into a RAM 207. The operation console 200 is further equipped with a communication interface 211 and is connected to a network so as to be capable of downloading data and programs that exists in the network. The programs and data stored in the various mediums such as the CD-ROM and the like, and the programs (including an image processing program) and data downloaded from the network are loaded into the RAM 207 and executed.

Figure 2:
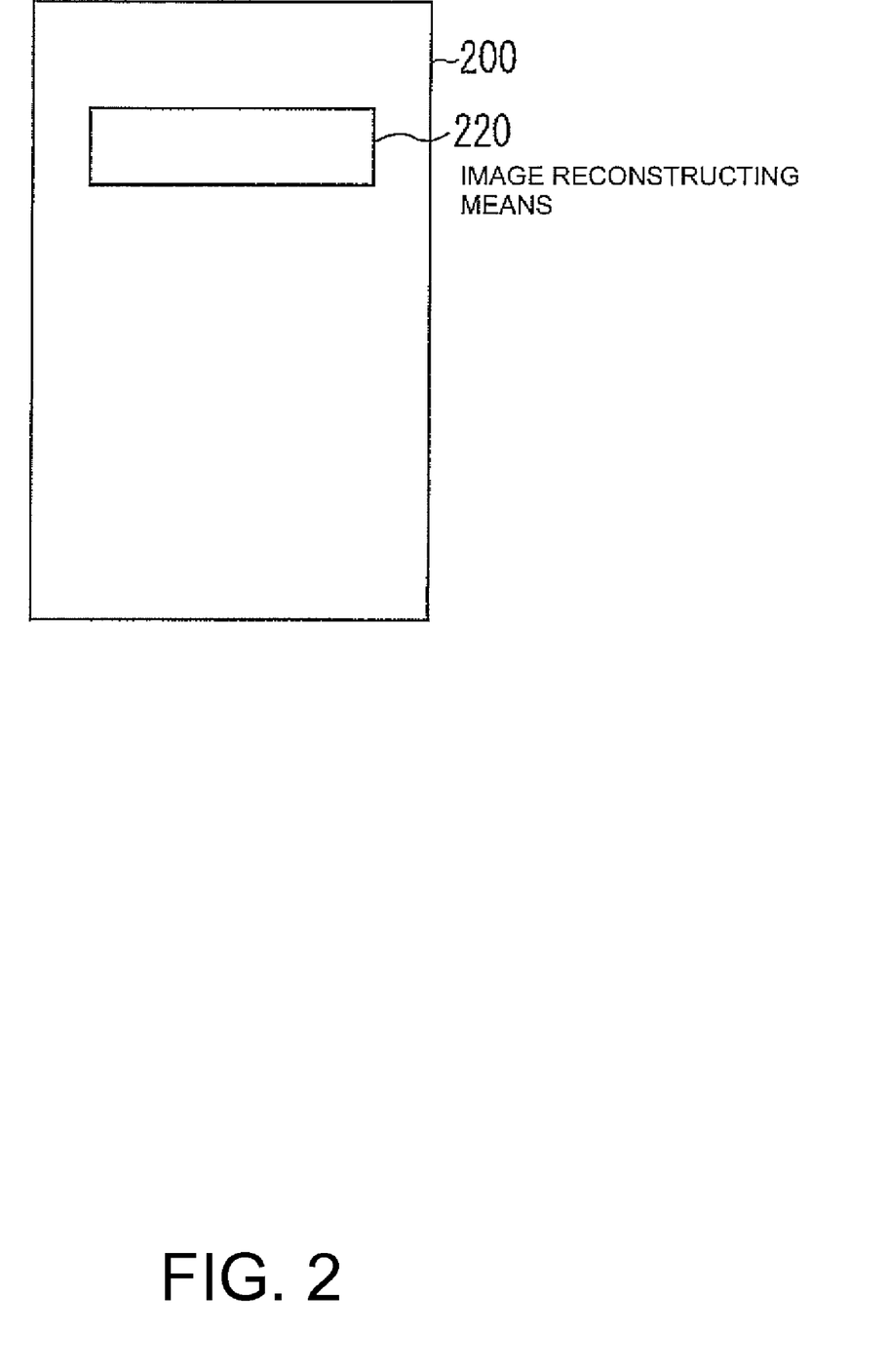
FIG. 2 is a block schematic diagram of an operation console employed in the embodiment.

FIG. 2 is a block diagram showing the function of the operation console 200. Image reconstructing device 220 of the present invention is configured by a computer that executes an image reconstructing process in the operation console.

An X-ray irradiation space is formed in a space defined inside a cylindrical structure of the scan gantry 120. The subject (patient) placed on the cradle 142 of the holding table 143 is carried in the X-ray irradiation space. An image of the subject 150 is projected onto the detector array 131 by the conebeam X-ray 400. X rays transmitted through the subject 150 are detected by the detector array 131.

An X-ray irradiation/detection device comprising the X-ray tube 124, collimator 127 and detector array 131 rotates about the body axis of the subject while their correlation is being held, thereby to perform a scan.

Figure 3:
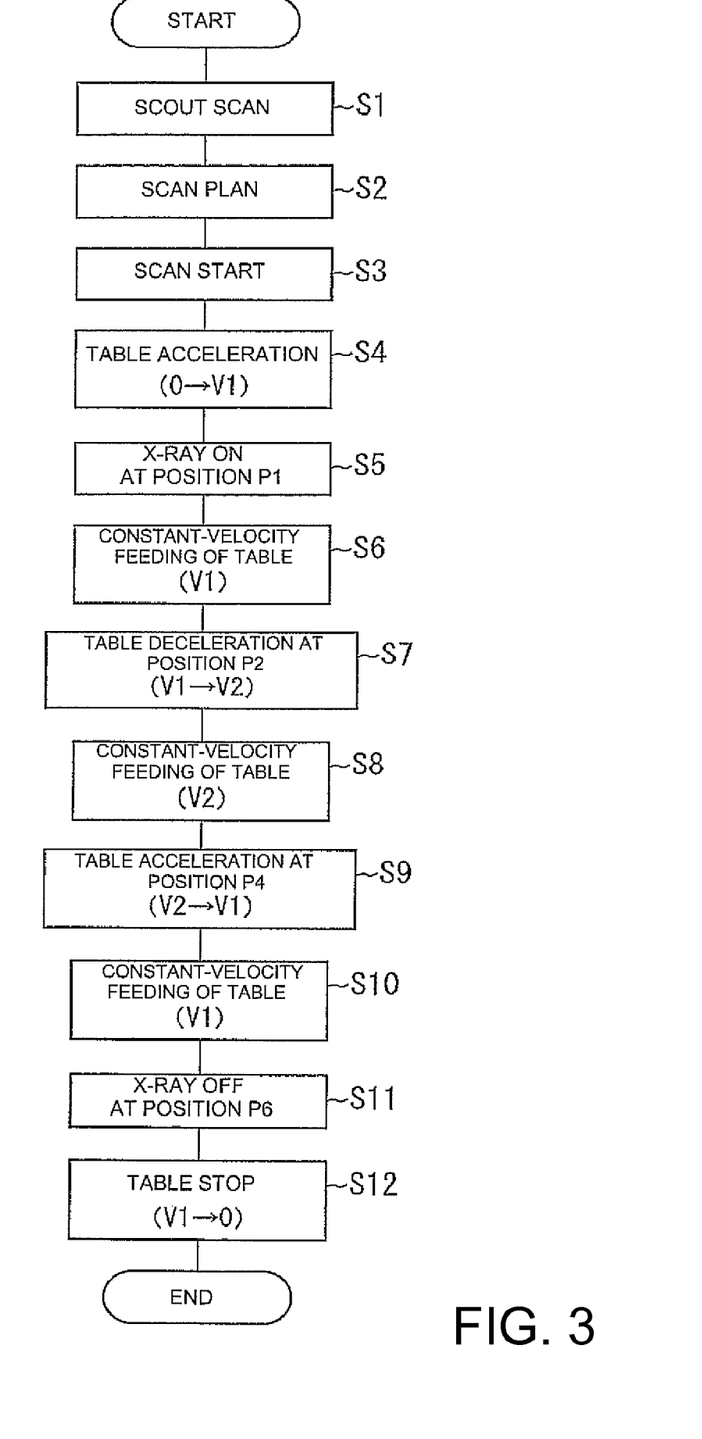
FIG. 3 is a flowchart showing the operation of the X-ray CT apparatus according to the embodiment.

FIG. 3 is a flowchart showing the operation of the scan device 100 of the X-ray CT apparatus 1000 according to the present embodiment. A scout scan is first performed in accordance with step S1. In the scout scan, for example, the subject is obtained or imaged from one direction or two directions without rotating an X-ray irradiation/detection system. Such a penetrated image is called "Scout image".

Next, a scan plan is created at step S2. The creation of the scan plan is performed in the form of interaction with the CPU 205 via the display device 202 and the input device 203. That is, the scout image obtained by the scout scan is displayed on the display device 202. A range for performing a helical scan and the feed velocity of the imaging table 140 are set onto its displayed image by the operator. Further, a slice thickness, an X-ray intensity and other photographic or imaging conditions are set.

Figure 4:
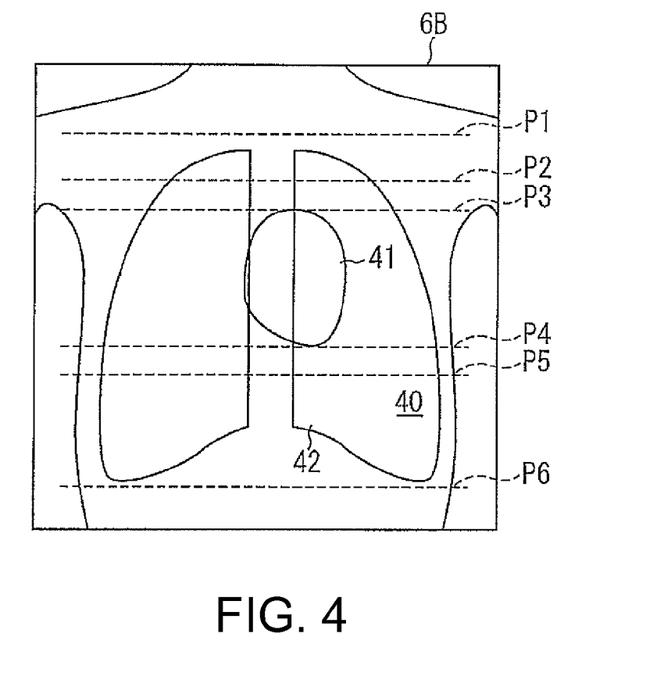
FIG. 4 is a diagram for describing the setting of positions according to the embodiment.

In the present embodiment, when a chest area 40 including the heart 41 and the lungs 42 is obtained or imaged, a helical scan start position P1 and a helical scan end position P6 are respectively set onto a scout image of a lung field 6B displayed on the display screen of the display device 202 as shown in FIG. 4 by way of example. The positions of P2, P3, P4 and P5 are respectively set in a helical scan range to specify or identify a range (first imaging range) of P3 to P4 excluding or not including the heart and specify between positions P1 and P2 corresponding to a range (second imaging range) including the heart, between positions P5 and P6 corresponding thereto, between positions P2 and P3 corresponding to a range (third imaging range) lying therebetween and between positions P4 and P5 corresponding thereto.

Here, the position P2 where deceleration is started is automatically calculated from an imaging condition for the heart and an imaging condition for the lungs. Described specifically, assuming that a coordinate position (hereinafter also called "Z position") of P2 in a Z-axis direction is Zp2, a Z position of P3 is Zp3, the acceleration of the table 140 is −αt, the velocity of the table 140 at the heart imaging is V2 and the velocity of the table 140 at the lung imaging is V1, Zp2 corresponding to the Z position of P2 is determined by the following Equation (1):

$$Zp2 = Zp3 - (V1 - V2)(V1 + V2)/2\alpha t \qquad \text{Eq. (1)}$$

Similarly, the position P5 where acceleration is completed, is automatically calculated from the imaging condition for the heart and the imaging condition for the lungs. Described specifically, assuming that a Z position of P4 is Zp4, a Z position of P5 is Zp5, the acceleration of the table 140 is αt, the velocity of the table 140 at the heart imaging is V2 and the velocity of the table 140 at the lung imaging is V1, Zp5 corresponding to the Z position of P5 is determined by the following Equation (2):

$$Zp5 = Zp4 + (V1 - V2)(V1 + V2)/2\alpha t \qquad \text{Eq. (2)}$$

According to another method, the position P2 where deceleration is started and the position P5 where acceleration is completed are set by their designation of the operator.

Figure 5:
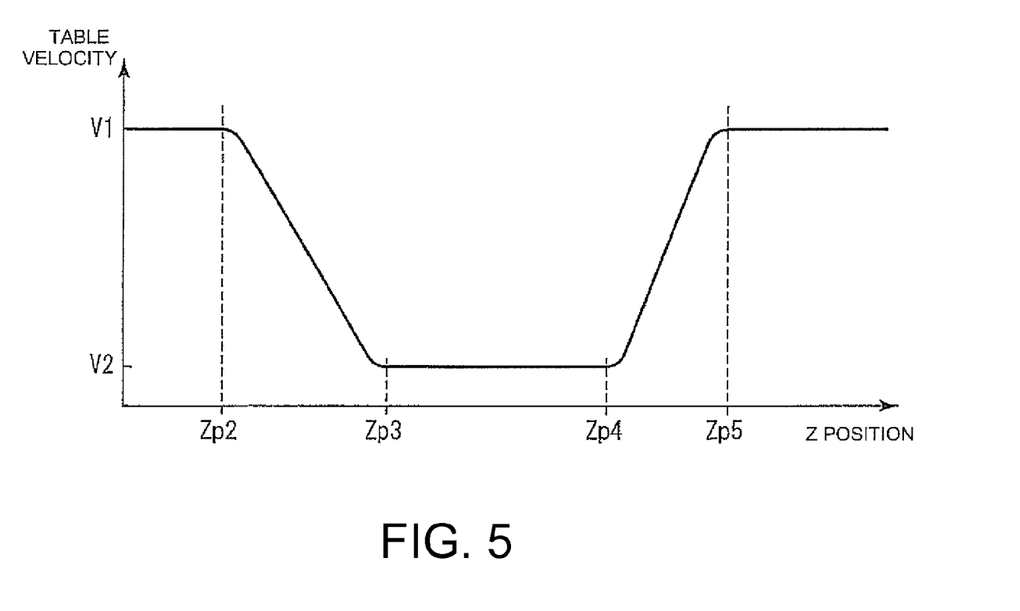
FIG. 5 is a graph showing a feed velocity at each Z position of a imaging table.

With such cutting-up, the helical scan range is divided into the five partial ranges, and the feed velocity of the imaging table 140 is controlled every partial range. FIG. 5 is a graph showing the feed velocity of the imaging table 140 at each Z position. As shown in the figure, a fast feed velocity V1 for lung imaging is set to the range from the imaging start position P1 and the velocity change position (deceleration start position) P2. In the range between the deceleration start position P2 and the deceleration completion position P3 (helical pitch 1.3, for example), deceleration is done at predetermined acceleration. A slow feed velocity V2 for heart imaging is set to the range from the deceleration completion position P3 to the acceleration start position P4. In the range from the acceleration start position P4 to the acceleration completion position P5, acceleration is done at predetermined acceleration. The fast feed velocity V1 is set again to the range from the acceleration completion position P5 to the imaging completion position P6.

Referring back to FIG. 3, a scan is started at step S3. Thus, the gantry rotating section 132 starts to rotate at a constant velocity. Next, the imaging table 140 is accelerated at step S4. Thus, the imaging table 140 starts to move at the velocity V1.

Next, at step S5, the application of X rays is started at the start position P1 (X-ray on). Thus, the acquisition of projection data about the subject by the helical scan is started from the start position P1.

Next, at step S6, the constant-velocity feeding of the imaging table 140 at the velocity V1 is performed up to the deceleration start position P2. Thus, a helical scan with the feed velocity in the body-axis direction as V1 is carried out.

Next, at step S7, the deceleration of the feed velocity of the imaging table 140 is done at the deceleration start position P2, and the imaging table 140 is decelerated up to V2 at the deceleration completion position P3. Next, at step S8, the constant-velocity feeding of the imaging table 140 at the velocity V2 is done up to the acceleration start position P4. Thus, a helical scan with the feed velocity in the body-axis direction as V2 is carried out.

Next, at step S9, the feed velocity of the imaging table 140 is accelerated at the acceleration start position P4 and reaches V1 at the acceleration completion position P5. Next, at step S10, the constant-velocity feeding of the imaging table 140 at the velocity V1 is done again from the acceleration completion position P5. Thus, a helical scan with the feed velocity in the body-axis direction as V1 is carried out.

Next, at step S11, the application of X rays is stopped at the end position P6 (X-ray off). Next, at step S12, the imaging table 140 is stopped and the scan is ended.

A description will next be made of the amount of data used for image reconstruction of a tomographic image at each position continued in the Z-axis direction upon image reconstruction using the X-ray projection data acquired by the scan device 100. Incidentally, the image reconstruction method using the X-ray projection data acquired by the known helical scan will be used in the present embodiment except for the characteristics related to the amount of data to be described later.

In the present embodiment, the image reconstruction of a tomographic image of one slice is conducted using data corresponding to a full scan, equivalent to view data for an angular range of 360° during the constant-velocity feed section (i.e., between the positions P1 and P2 and between the positions P5 and P6) at V1 corresponding to the second imaging range (full reconstruction). Thus, a high-quality image can be reconstructed at the fast feed velocity V1, efficiently and despite of a scan with less application of X rays. On the other hand, during a constant-velocity feed section (i.e., between the positions P3 and P4) at the velocity V2, corresponding to the first imaging range, the image reconstruction of one slice is done using data obtained while the gantry 120 is being rotated by an angle obtained by adding one fan angle (angle of detector width) 2γm to a half turn 58 (i.e., 180°) (half reconstruction).

Incidentally, the X-ray projection data most suitable for the image reconstruction of a tomographic image of one slice corresponds to data obtained during a period in which a heartbeat cycle is closest to the cessation. The period is selected by paying attention to the fact that the heart of a human being is indicative of a minimum movement during a period from the time where the heart is almost filled with the blood to a heart contraction time corresponding to the time when the heart muscle contracts rapidly to pump the blood. In order to assuredly acquire X-ray projection data about the heart during the period in which the heart is closest to the cessation, the X-ray CT apparatus 1000 generates or creates desired data using data from a segment corresponding to the portion where the heartbeat is closest to the cessation.

The segment data corresponding to the portion where the heartbeat is closest to the cessation can be specified using the known method. Described specifically, the point of time when a predetermined time has elapsed after the detection of an R peak can be defined as a segment data start point, and the point of time when the time taken to cause the gantry 120 to rotate by a half scan has elapsed can be defined as a segment data end point. In one embodiment of the present application, the operation console 200 of the X-ray CT system 1000 analyzes an ECG (Electrocardiogram) signal and controls the X-ray tube controller 123 in such a manner that X rays are not applied during a time interval at which the heart is not at rest.

Next, such an amount of data that the amount of data used for the image reconstruction changes gradually is used in the third imaging range, i.e., the range for switching between the first imaging range and the second imaging range.

Figure 6:
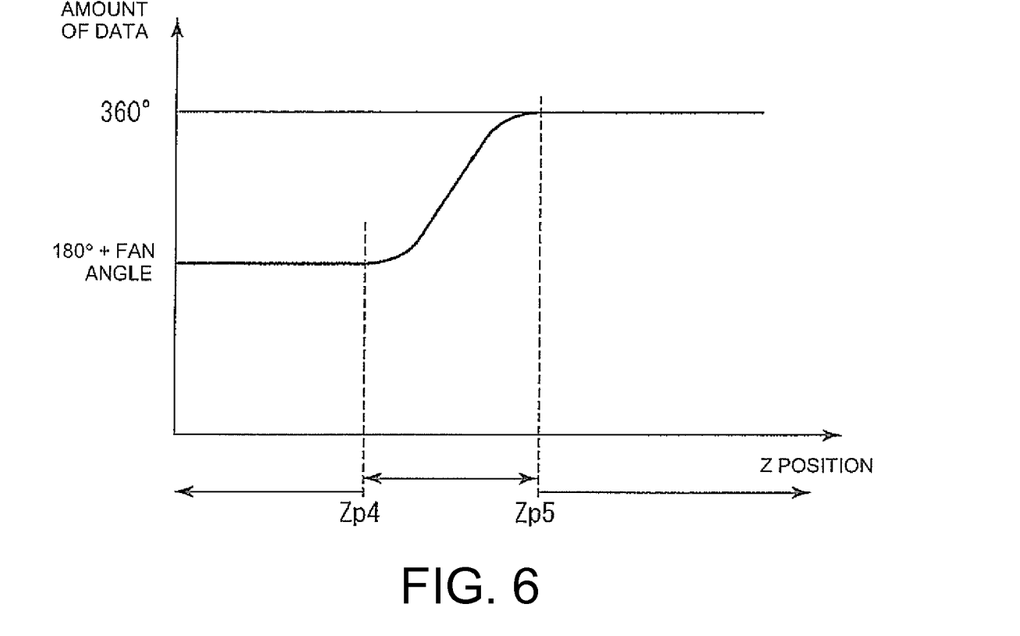
FIG. 6 is a graph illustrating a variation in the amount of data used for image reconstruction according to the embodiment.
Figure 7:
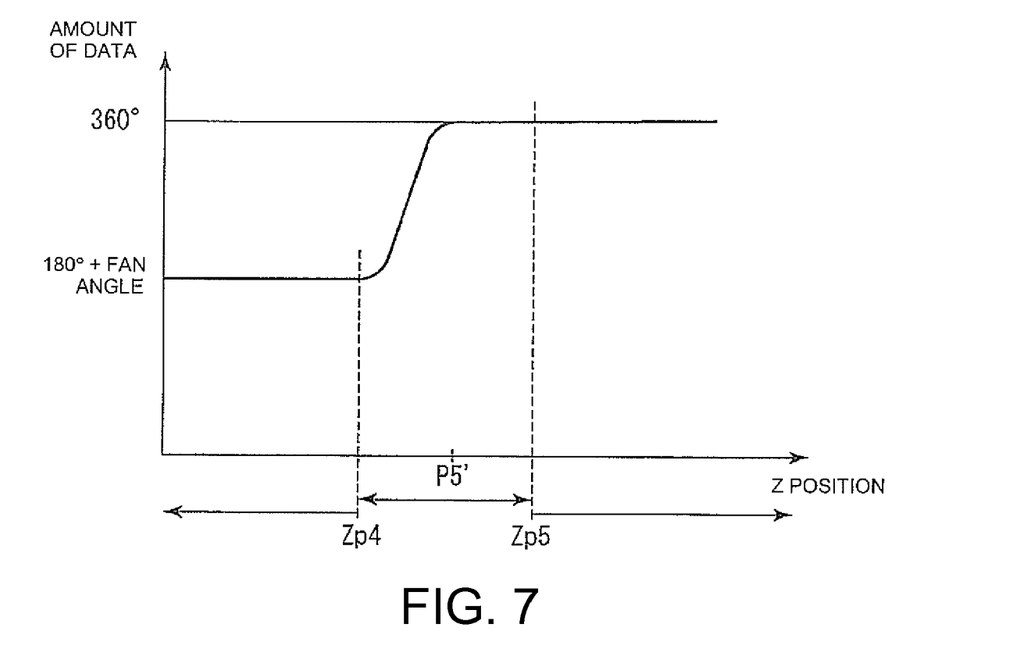
FIG. 7 is a graph showing a variation in the amount of data used for the image reconstruction according to another embodiment.

FIGS. 6 and 7 are graphs showing a variation in the used amount of data. As shown in FIGS. 6 and 7, such an amount-of-data calculation function that the amount of data gradually changes from the amount of data corresponding to a half scan to the amount of data corresponding to a full scan is applied between the positions P4 and P5.

Described specifically, an image reconstruction algorithm (reproduced pixel value) using projection data is given as expressed by Equations (3) and (4):

$$\tilde{f}(x, y, z) = \frac{\pi}{(\beta\max - \beta\min)} \qquad \text{Eq. (3)}$$

$$\int_{\beta\min}^{\beta\max} \frac{Fi}{\sqrt{(Fi)^2 + Z^2}} \omega_{3d}(\alpha, \beta, D_\gamma) \tilde{s}(\alpha, \beta, D_\gamma) d\beta$$

$$\tilde{s}(\alpha, \beta, D_\lambda) = s(\alpha, \beta, D_\gamma) \otimes g(t) \qquad \text{Eq. (4)}$$

where $\omega_{3d}(\alpha, \beta, D_\gamma)$ indicates a three-dimensional weight including weights of a cone angle α, a view angle β and channel data $D_\gamma$. Fi indicates the distance between the focal point of the X-ray tube and an ISO center. βmax−βmin indicates a view angular range of data used for image reconstruction, and Z indicates the distance in a Z direction as viewed from the center of a detector. g(t) indicates a reconstruction Kernel.

In Equation (3), βmax−βmin=π+2γm is given as the view angular range of the data used for image reconstruction in the case of the half scan. βmax−βmin=2π is given as the view angular range in the case of the full scan. In the third imaging range, the amount of data is determined in accordance with an amount-of-data calculation function curve shown in FIG. 6, thereby assuming π+2γm<βmax−βmin<2π. As is apparent by those skilled in the art, when projection data by a helical scan is backprojected to reconstruct a slice image, the midpoint between βmax and βmin can be determined corresponding to a Z position of a slice to be reconstructed. If the angular range of βmax−βmin is decided, then βmax and βmin can be determined.

An amount-of-data calculation function for calculating the amount of data in the third range can be expressed as two quadratic curves in which when Z=Zp4 and Z=Zp5, for example, a differential value becomes 0 and the two are continuous. The two quadratic curves can be defined as follows in Equations (5) and (6):

$$\beta\max-\beta\min=(z-Zp4)^2/(\pi-2\gamma m)+\pi+2\gamma m \text{ (when } Zp4<z\leq(Zp4+Zp5)/2) \qquad \text{Eq. (5)}$$

$$\beta\max-\beta\min=2\pi-(z-Zp5)^2/(\pi-2\gamma m) \text{ (when } (Zp4+Zp5)/2<z<Zp5) \qquad \text{Eq. (6)}$$

The amount-of-data calculation function may be a function for gently changing the difference between the amounts of data used in the first imaging range and the second imaging range in the third imaging range. Various functions such as a linear curve, a sine (cosine) curve, a multidimensional curve, a sigmoid curve, etc. can be applied. As well as the calculation by the function, the amount of data between the amount of data for the first imaging range and the amount of data for the second imaging range may be allocated at suitable intervals depending on the number of tomographic images included in the third imaging range so as to assume a suitable interval.

Although the amount-of-data calculation function in the range of switching from the second imaging range to the first imaging range has been described above, the amount of data used for image reconstruction can gradually be changed from the amount of data corresponding to the full scan to the amount of data corresponding to the half scan by application of a function linearly symmetrical to the amount-of-data calculation function of FIG. 6 similarly even in the range of switching from the first imaging range to the second imaging range.

Although the variable velocity portion of the imaging table 140 and the switching range are caused to coincide with each other in the example shown in FIG. 6, it is not necessary to cause the two to coincide with each other. FIG. 7 is a graph showing one example of an amount-of-data calculation function in which the two do not coincide with each other. As shown in the figure, the switching range is ended at P5' closer to the acceleration start position P4 than the acceleration completion position P5. Image reconstruction based on the full reconstruction is performed between P5' and P5. Thus, tomographic images using data higher in image quality, corresponding to the full scan can be obtained between P2 and P3 and between P4 and P5. Although the amount-of-data calculation function in the range of switching from the second imaging range to the first imaging range has been described in FIG. 6, the amount of data used for image reconstruction can be changed from the amount of data corresponding to the full scan to the amount of data corresponding to the half scan by application of a function linearly symmetrical to the amount-of-data calculation function of FIG. 6 similarly even as to the range of switching from the first imaging range to the second imaging range.

According to the above embodiment, since the image quality such as noise characteristics caused by the amount of data used for the image reconstruction of each tomographic image gradually changes between the tomographic images in the third imaging range, a sudden change in the image quality can be prevented between the tomographic image in the first imaging range and the tomographic image in the second imaging range. As a result, the boundary due to the sudden change in the image quality can be prevented from occurring when the three-dimensional image or the like using the plural continuous tomographic images is generated.

The achievement of various necessity satisfied by the present invention has been explained by exemplifying the various embodiments of the present invention. It should however be understood that these embodiments are mere illustrations of the principles of various embodiments of the present invention. Many changes to such various embodiments as not to depart from the gist and scope of the present invention and their adaptive configurations will be apparent to those skilled in the art. Although the form in which the feed velocity of the imaging table is changed has been explained in the embodiment in particular, the invention of the present application can be implemented even in the case where the feed velocity of the imaging table is constant. Although a description has been made of the case where the full reconstruction and the half reconstruction are respectively performed in the first imaging range and the second imaging range, the present invention can be applied to the case where image reconstruction is performed using the amounts of data respectively different from each other. For example, the amounts of data respectively different from one another selected from view data from an angular range of 180°+fan angle to an angular rage of 360° may be adopted as well as the amount of data corresponding to the scan and the amount of data corresponding to the half scan. Alternatively, the amount of data corresponding to an angular range of 360° or more may be used.

The present invention is applicable not only to the inspection of a human body and plants and animals but also to the inspection of the inside state of a machine, for example. The X-ray CT apparatus described in the present specification is of "a third-generation" apparatus in which both of an X-ray source and a detector rotate together with a gantry. Other many X-ray CT apparatuses such as "a fourth-generation" apparatus in which a detector remains stationary in full ring form and only an X-ray source rotates together with a gantry, can also be used. All the modifications will be included in the present specification. Thus, the present invention will cover all suitable changes and modifications such as included within the claims and the scope of equivalents.

What is claimed is:

1. An X-ray CT apparatus comprising:
a scan device comprising:
an X-ray source;
an X-ray detection unit configured to detect X-rays irradiated from said X-ray source, said X-ray detection unit comprising a plurality of detector elements;
an imaging table for placing a subject thereon and configured to dispose the subject between said X-ray source and said X-ray detection unit;
a controller configured to control irradiation of the subject with X-rays from said X-ray source while said imaging table, said X-ray source, and said X-ray detection unit are relatively moved along a body axis of the subject;
an X-ray data acquisition section configured to acquire projection data of the X-rays detected by said X-ray detection unit; and
an image reconstructing device configured to:
specify a first imaging range, a second imaging range, and a third imaging range located between the first imaging range and the second imaging range, in association with a position on the body axis of the subject;
image-reconstruct a first tomographic image included in the first imaging range using a first projection data amount corresponding to an amount of projection data necessary for image reconstruction of the first tomographic image;
image-reconstruct a second tomographic image included in the second imaging range using a second projection data amount less than the first projection data amount and corresponding to an amount of projection data necessary for image reconstruction of the second tomographic image; and
image-reconstruct a third tomographic image included in the third imaging range using a third projection data amount less than the first projection data amount and greater than the second projection data amount.

2. The X-ray CT apparatus according to claim 1, wherein the second range is a range including the heart of the subject, and the first range is a range not including the heart.

3. The X-ray CT apparatus according to claim 1, wherein the amount of projection data necessary for the image reconstruction of each of the first, second, and third tomographic images is an amount of projection data selected from view data from an angular range of 180°+fan angle to an angular range of 360°.

4. The X-ray CT apparatus according to claim 3, wherein the first projection data amount is view data corresponding to the angular range of 360°, and the second projection data amount is view data corresponding to the angular range of 180°+fan angle.

5. The X-ray CT apparatus according to claim 1, wherein the third projection data amount is set in such a manner that the third tomographic image included in the third imaging range is provided in plural form and the amount of projection data decreases continuously from the first range side to the second range side at the tomographic images.

6. The X-ray CT apparatus according to claim 1, wherein said controller is configured to control the movement of said imaging table relative to said X-ray source and said X-ray detection unit at a velocity V1 in the first range, control the relative movement at a velocity V2 different from the velocity V1 in the second range, and to control the relative movement by acceleration or deceleration from the velocity V1 to the velocity V2 or from the velocity V2 to the velocity V1.

7. The X-ray CT apparatus according to claim 6, wherein said controller is configured to control the movement of said imaging table relative to said X-ray source and said X-ray detection unit at a velocity V1 in the first range, and to control the relative movement at a velocity V2 lower than the velocity V1 in the second range.

8. The X-ray CT apparatus according to claim 1, wherein the first range, the second range and the third range are specified based on a pre-acquired scout image of the subject.

9. The X-ray CT apparatus according to claim 8, wherein the first range corresponds to each of ranges related to the second range, which adjoin both sides of the subject as viewed in the direction of the body axis thereof.

10. An image reconstructing device configured to image-reconstruct a plurality of tomographic images of a subject based on projection data acquired using an X-ray CT apparatus, wherein said image reconstructing device is further configured to:
   image-reconstruct a first tomographic image included in a first imaging range using a first projection data amount corresponding to an amount of projection data necessary for image reconstruction of the first tomographic image;
   image-reconstruct a second tomographic image included in a second imaging range using a second projection data amount less than the first projection data amount and corresponding to an amount of projection data necessary for image reconstruction of the second tomographic image; and
   image-reconstruct a third tomographic image included in a third imaging range using a third projection data amount less than the first projection data amount and greater than the second projection data amount, wherein the first imaging range, the second imaging range, and the third imaging range located between the first imaging range and the second imaging range are specified in association with a position on a body axis of the subject.

11. The image reconstructing device according to claim 10, wherein the second range is a range including the heart of the subject, and the first range is a range not including the heart.

12. The image reconstructing device according to claim 10, wherein the amount of projection data necessary for the image reconstruction of the plurality of tomographic images is an amount of projection data selected from view data from an angular range of 180°+fan angle to an angular range of 360°.

13. The image reconstructing device according to claim 12, wherein the first projection data amount is view data corresponding to the angular range of 360°, and the second projection data amount is view data corresponding to the angular range of 180°+fan angle.

14. The image reconstructing device according to claim 10, wherein the third projection data amount is set in such a manner that the tomographic image included in the third imaging range is provided in plural form and the amount of projection data decreases continuously from the first range side to the second range side at the tomographic images.

15. The image reconstructing device according to claim 10, wherein the X-ray CT apparatus controls so as to perform the movement of the imaging table relative to the X-ray source and the X-ray detection unit at a velocity V1 in the first range, performs the relative movement at a velocity V2 different from the velocity V1 in the second range, and performs the relative movement by acceleration or deceleration from the velocity V1 to the velocity V2 or from the velocity V2 to the velocity V1.

16. The image reconstructing device according to claim 15, wherein the X-ray CT apparatus controls so as to performs the movement of the imaging table relative to the X-ray source and the X-ray detection unit at a velocity V1 in the first range, and performs the relative movement at a velocity V2 lower than the velocity V1 in the second range.

17. The image reconstructing device according to claim 10, wherein the first range, the second range and the third range are specified based on a pre-acquired scout image of the subject.

18. The image reconstructing device according to claim 17, wherein the first range corresponds to each of ranges related to the second range, which adjoin both sides of the subject as viewed in the direction of the body axis thereof.

19. An X-ray CT imaging method comprising:
   detecting X-rays irradiated from an X-ray source through a subject;
   acquiring projection data of the detected X-rays;
   specifying a first imaging range, a second imaging range, and a third imaging range located between the first imaging range and the second imaging range, in association with a position on a body axis of the subject;
   image-reconstructing a first tomographic image included in the first imaging range using a first projection data amount corresponding to an amount of projection data necessary for image reconstruction of the first tomographic image;
   image-reconstructing a second tomographic image included in the second imaging range using a second projection data amount less than the first projection data amount and corresponding to an amount of projection data necessary for image reconstruction of the second tomographic image; and
   image-reconstructing a third tomographic image included in the third imaging range using a third projection data amount less than the first projection data amount and greater than the second projection data amount.

20. An X-ray CT imaging method according to claim 19, wherein the second range is a range including the heart of the subject, and the first range is a range not including the heart.

* * * * *